United States Patent [19]

Thornfeldt

[11] Patent Number: 5,219,880
[45] Date of Patent: Jun. 15, 1993

[54] TREATMENT OF VIRAL TUMORS AND HEMORRHOIDS WITH ARTEMISININ AND DERIVATIVES

[75] Inventor: Carl R. Thornfeldt, Ontario, Oreg.

[73] Assignee: Dermatologic Research Corporation, Novato, Calif.

[21] Appl. No.: 677,065

[22] Filed: Mar. 29, 1991

[51] Int. Cl.⁵ .......................................... A61K 31/335
[52] U.S. Cl. .................................................. 514/450
[58] Field of Search ........................................ 514/450

[56] References Cited

U.S. PATENT DOCUMENTS

| 4,978,676 | 12/1990 | Thornfeldt | 514/450 |
| 5,057,501 | 10/1991 | Thornfeldt et al. | 514/53 |

OTHER PUBLICATIONS

World Health Organization, "The Development of Artemisinin and Its Derivatives: Report of a Meeting of the Scientific Working Group on the Chemotherapy of Malaria", Geneva, Switzerland, Oct. 6–7, 1986.

Klayman, D. L., "Qinghaosu (Artemisinin): An Antimalarial Drug from China", Science, vol. 228, May 31, 1985.

Krungkrai, S. R., et al., "The Antimalarial Action of Plasmodium Falciparum of Qinghaosu and Artesunate in Combination with Agents which Modulate Oxidant Stress", Transactions of The Royal Society of Tropical Medicine and Hygiene (1987), 81, 710–714.

Primary Examiner—Jerome D. Goldberg

[57] ABSTRACT

Hemorrhoids and viral-induced skin tumors such as warts and molluscum contagiosum are successfully treated with topical administration of artemisinin, dihydroartemisinin, its semisynthetic derivatives and its synthetic analogs.

7 Claims, No Drawings

TREATMENT OF VIRAL TUMORS AND HEMORRHOIDS WITH ARTEMISININ AND DERIVATIVES

BACKGROUND OF THE INVENTION

This invention relates to the topical and/or systemic treatment of viral-induced skin tumors and hemorrhoids with a class of compounds having sesquiterpene structures, including artemisinin, dihydroartemisinin, and derivatives and analogs of these compounds.

Currently known treatments of viral-induced tumors such as warts and molluscum contagiosum suffer from being sometimes ineffective and usually painful. The wart (papova) virus produces hypertrophic viable cells in the tumor mass and suppresses skin cellular immunity against the virus.

Hemorrhoids are the end result of swelling and inflammation of anorectal veins. Current treatments consist of topical analgesics and antiinflammatory agents as well as cathartics. Surgery often is curative but is extremely painful and requires prolonged convalescence.

Artemisinin or Qinghaosu is a proven systemic antimalarial agent purified from the herb Artemisia Annua. Artemisinin is a sesquiterpene lactone with a peroxide grouping that is water insoluble but is extremely safe. There are reports from China that artemisinin 1) is virustatic against influenza virus in chick embryo, 2) suppresses humoral immunity, 3) stimulates cell mediated immunity, and 4) inhibits protein and DNA synthesis thus halting hypertrophy and hyperproliferation of cells. A tea made from the herb Artemisia Annua was used for centuries to treat hemorrhoids, malaria and other maladies.

In an effort to improve water solubility and decrease recurrences, scientists have developed semisynthetic derivatives and synthetic analogs of artemisinin. These compounds display the aforementioned sought-after characteristics with the added benefit of increased antimalarial activity. These compounds have never been studied for therapeutic activity in any primary skin diseases or tumors, and along with artemisinin have never been used as a topical treatment for any disease.

Treating primary skin disease and tumors with topically applied drugs improves safety, therapeutic success, and is much more cost effective. All topical drugs must penetrate the stratum corneum "barrier" to be effective. Since very few drugs successfully penetrate the stratum corneum by themselves, penetration enhancers or vehicles have been developed to cross this barrier. When combined with the active drug, a dramatic improvement in therapeutic effectiveness occurs.

SUMMARY OF THE INVENTION

It has been discovered that compounds having structures which contain sesquiterpene groups are effective therapeutic agents useful in the treatment of warts, molluscum contagiosum and hemorrhoids.

The compounds which are discovered to have these properties, in accordance with this invention, include artemisinin; dihydroartemisinin; carbonate, sulfonate, ester, and ether derivatives of dihydroartemisinin, notably artemether, artesunate and artesunate salts, and dihydroartemisinin propyl carbonate; as well as the bis-ether artelinic acid. In the practice of the invention, formulations of these compounds are administered topically. The compounds are preferably formulated with vehicles which enhance the penetration of the formulations through the stratum corneum.

DETAILED DESCRIPTION OF THE INVENTION AND PREFERRED EMBODIMENTS

The compounds applied in accordance with the present invention are generally those whose molecular formulas include a sesquiterpene structure, preferably a sesquiterpene lactone with an attached peroxide. Within this group, those which are particularly preferred are artemisinin, dihydroartemisinin, semisynthetic derivatives of dihydroartemisinin including propyl carbonate dihydroartemisinin, artemether, artesunate, and other ethers, esters, carbonates and sulfonates, and the synthetic analog, artelinic acid.

The compounds used in the present invention include those falling within the following generic formula:

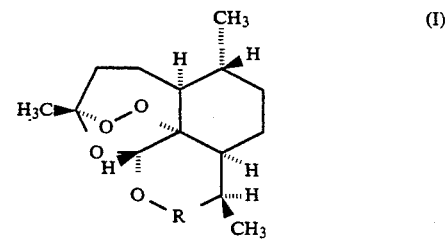

where R is either

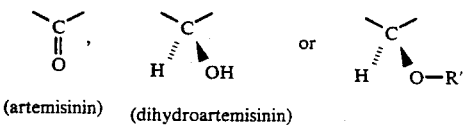

(artemisinin)    (dihydroartemisinin)

in which R' is as follows:

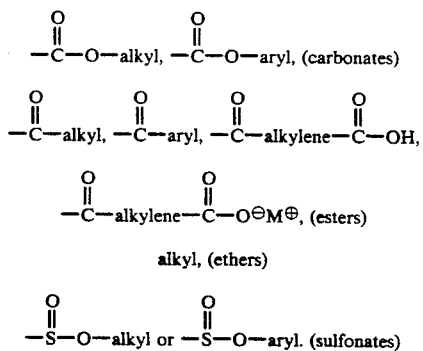

alkyl, (ethers)

In the R' definition, the terms "alkyl" and "alkylene" preferably refer to lower alkyl or alkylene groups, notably $C_1$-$C_6$, with $C_1$-$C_4$ most preferred. Straight-chain and branched-chain groups are included, with straight-chain groups preferred. The term "aryl" preferably refers to phenyl and naphtyl, with phenyl the most preferred. The symbol M in Formula I is an alkali or alkaline earth metal, preferably sodium or potassium, with sodium the most preferred. The ester in which R' is —C(O)—(CH$_2$)$_2$—CO$_2$H is known by the common names artesunic acid and artesunate, and the ester in which R' is —C(O)—(CH$_2$)$_2$—CO$_2$ $^\ominus$Na$^\oplus$ is known as sodium artesunate.

Also included is the bis-ether, artelinic acid, having the formula:

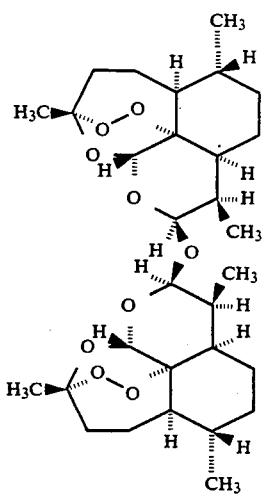
(II)

The concentrations of the sesquiterpene structure compounds in the formulations to be applied in the practice of the present invention are not critical and may vary widely. In most applications, however, best results will be obtained using formulations containing the compounds at levels of from about 0.01% to about 35% by weight, preferably from about 0.5% to about 15%. The amount of the compound actually administered for treatment will be therapeutically effective amount, which term is used herein to denote the amount needed to produce a substantial clinical improvement. Optional amounts will vary with the method of administration, and will generally be in accordance with the amounts of conventional medicaments administered in the same or a similar form. Topical application, for instance, is typically done from once to three times a day.

The topical formulations may further include one or more of the wide variety of agents known to be effective as skin penetration enhancers. Examples of these are 2-pyrrolidone, N-methyl-2-pyrrolidone, dimethylacetamide, dimethylformamide, propylene glycol, alcohol, dimethyl sulfoxide, and Azone. Additional agents may further be included to make the formulation cosmetically acceptable. Examples of these are fats, waxes, oils, dyes, fragrance, preservatives, stabilizers, and surface active agents. Keratolytic agents such as those known in the art may also be included. Examples are salicylic acid, sulfur, trans-retinoic acid and later generations of retinoids. The amounts of each of these various types of additive will be readily apparent to those skilled in the art, optimal amounts being the same as in other, known formulations designed for the same type of administration. Stratum corneum penetration enhancers, for example, will typically be included at levels within the range of about 0.1% to about 30% by weight, preferably from about 1% to about 15%.

The following example is offered for purposes of illustration, and is intended neither to define nor limit the invention in any manner.

EXAMPLE

Three patients, each with one to three external hemorrhoids that did not respond to either Anusol H of Preparation H, were treated with an ointment containing 1% artemisinin by weight (with no penetration enhancers), with topical administration four times daily. In each case, itching, tenderness and swelling were relieved in all patients in four to six days.

The foregoing is offered primarily for purposes of illustration. It will be readily apparent to those skilled in the art that further variations in the formulations and uses of the compounds beyond those described herein may be made without departing from the spirit or scope of the invention.

What is claimed is:

1. A method for the treatment of a patient suffering from hemorrhoids, said method comprising topically administering to said patient a therapeutically effective amount of a compound having the formula

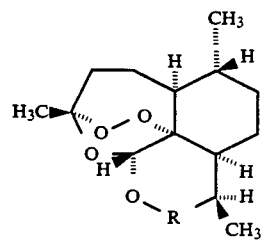

in which R is a member selected from the group consisting of

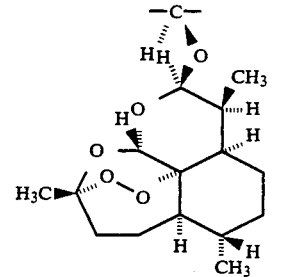

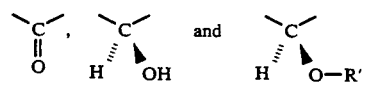

where R' is a member selected from the group consisting of

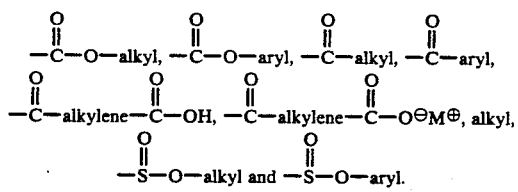

in which M is a member selected from the group consisting of sodium and potassium.

2. A method in accordance with claim 1 in which said compound is a synthetic analog of dihydroartemisinin.

3. A method in accordance with claim 1 in which said compound is artelinic acid.

4. A method in accordance with claim 1 in which said compound is a semisynthetic derivative of dihydroartemisinin selected from the group consisting of esters, ethers, carbonates and sulfonates.

5. A method in accordance with claim 1 in which said compound is a member selected from the group consisting of artemisinin, dihydroartemisinin, artemether, artesunate, and dihydroatemisinin propyl carbonate.

6. A method in accordance with claim 1 in which said compound is a member selected from the group consisting of artemisinin, dihydroartemisinin, artemether, artesunate, and dihydroartemisinin propyl carbonate; and said composition further contains a member selected from the group consisting of N-methyl-2-pyrrolidone and dimethylacetamide.

7. A method in accordance with claim 1 in which said compound is artemisinin.

* * * * *